(12) United States Patent
Li et al.

(10) Patent No.: US 10,467,741 B2
(45) Date of Patent: Nov. 5, 2019

(54) CT SIMULATION OPTIMIZATION FOR RADIATION THERAPY CONTOURING TASKS

(71) Applicant: Washington University in St. Louis, St. Louis, MO (US)

(72) Inventors: Hua Li, Chesterfield, MO (US); Sasa Mutic, Creve Coeur, MO (US); Mark Anastasio, St. Louis, MO (US)

(73) Assignee: Washington University, St. Louis, MO (US)

( * ) Notice: Subject to any disclaimer, the term of this patent is extended or adjusted under 35 U.S.C. 154(b) by 648 days.

(21) Appl. No.: 15/054,215

(22) Filed: Feb. 26, 2016

(65) Prior Publication Data

US 2016/0253443 A1    Sep. 1, 2016

Related U.S. Application Data

(60) Provisional application No. 62/121,166, filed on Feb. 26, 2015.

(51) Int. Cl.
*G06T 7/00* (2017.01)
*G06F 19/00* (2018.01)
*G16H 50/50* (2018.01)

(52) U.S. Cl.
CPC ............ *G06T 7/0002* (2013.01); *G06F 19/30* (2013.01); *G06T 2207/10081* (2013.01); *G16H 50/50* (2018.01)

(58) Field of Classification Search
CPC ..................... G06F 17/5009; G06G 17/11
See application file for complete search history.

(56) References Cited

U.S. PATENT DOCUMENTS

2011/0270623 A1* 11/2011 Reiner .................. G06F 19/321
                                                          705/2
2017/0259083 A1*  9/2017 Nakatsugawa ........ A61B 6/032

* cited by examiner

*Primary Examiner* — Benjamin P Sandvik
(74) *Attorney, Agent, or Firm* — Smith Gambrell & Russell LLP (57) ABSTRACT

A method for optimizing a CT simulation protocol for different size patients for contouring and segmentation of organs and tumors. The method scanning different size phantoms, cadavers, or patients with a CT scanning x-ray tube to create a set of images and to create data sets for each different size phantoms, cadavers, or patients and then calculating an image quality index (IQI) as a benchmark for contouring accuracy. Finding an optimal IQI that characterizes patients of different sizes and using the optimal IQI to determine the accuracy of the contouring and segmentation of A CT simulation protocol for a patient.

7 Claims, 11 Drawing Sheets

CT SIMULATION OPTIMIZATION FOR RADIATION THERAPY CONTOURING TASKS

CROSS REFERENCE TO RELATED PATENT APPLICATIONS

This invention claims priority from U.S. Provisional Patent Application No. 62/121,166, filed Feb. 26, 2015, which is hereby incorporated by reference.

FIELD OF THE INVENTION

The present invention relates to x-ray computed tomography (CT) scanning, and more particularly relates to an optimized CT simulation protocol based on the tasks of accurate contouring and segmenting tumors and organs from CT images of different size patients.

BACKGROUND OF THE INVENTION

The Centers for Disease Control and Prevention (CDC) reported that in 2010 approximately 40.5% of men aged 20-74 in the US were obese or morbidly obese while the rate of morbidly obese patients was 4.5%. The obesity rate is still rapidly growing. This demographic is mirrored in the radiation oncology patient population. The need for obese specific tools, such as heavier couch weight limits and large-bore CT simulators, are needed in part as a response to this changing demographic. In addition, CT simulation scans, the acquisition of a CT scan image for radiation treatment planning, is also impacted by patient obesity.

A CT simulation scan is used to define tumor and normal organ anatomy by segmenting the tumors and organs manually or by using commercial available semi-automated and automated techniques for segmenting tumors and organs. A physician develops a prescription that defines the tumor dose and dose limits to critical organs. The segmented targets for the tumors and organs are used to define the radiation beams and beam fluences in a treatment plan that is compared against the prescription to determine its clinical acceptability. Once approved, the plan parameters are transferred to a linear accelerator for delivery of treatment doses of radiation to the patient.

Accurate tumor volume (contour) and critical organ segmentations are critical for maximizing tumor conformality. Tumor contour and organ segmentation primarily depend on tumor and critical structure CT conspicuity, interpretation of radiological anatomy, and understanding of the potential areas of tumor involvement based on tumor biology with a central assumption that CT-based target segmentation provides an accurate patient anatomy description. CT simulation scanning is the standard of care in radiation therapy for the simulation of prostate cancer patients, and will likely remain so for the foreseeable future. CT simulation scanning is the standard of care because of its availability, large bore size, fast acquisition, high geometrical accuracy, and direct connections to electron density used for radiation dose calculations. CT simulation scans are used to provide quantitative target and structure segmentation for accurate radiation treatment planning.

Figure 2A:
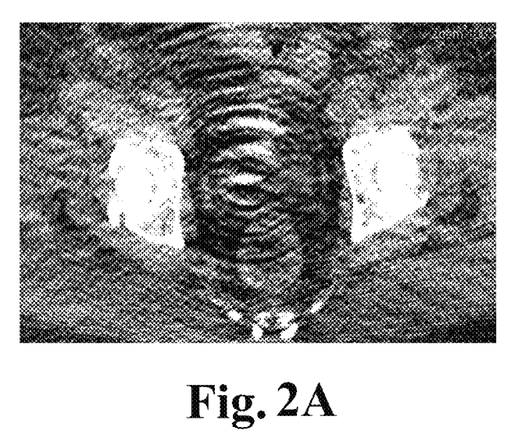
FIG. 2A is an x-ray image of the prostate region of an obese patient resulting from a CT scan having a radiation dosage value of 67.2 mGy.
Figure 2B:
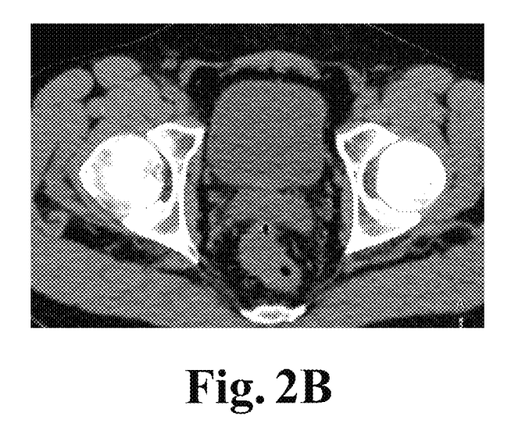
FIG. 2B is an x-ray image of the prostate region of a thin patient resulting from a CT scan having a radiation dosage value of 18.2 mGy.

Conventionally, CT simulation scans and scanning equipment are designed based on the underlying assumptions used to design the CT diagnostic protocols. Such design assumptions, however, may not match those in the radiation oncology workflow, especially for obese prostate cancer patients. At present, default CT simulation protocols for obese prostate cancer patients are revised by increasing the amperage (mAs) of the x-ray tube. The limitation of this approach is that, while increased mAs have an impact on image quality, increased amperage, as shown in FIG. 2 may be insufficient for some patients, especially obese patients. FIG. 2 shows examples of clinical treatment planning CT scans from obese (a) and thin (b) prostate cancer patients having lateral pelvis diameters of 60 centimeters (cm) and 33 cm, respectively. The image of the thin patient (FIG. 2b) clearly shows the prostate and bladder, while the image of the obese patient (FIG. 2a) contains high noise levels and residual photon starvation artifacts, degrading the image quality to the extent that the prostate and bladder are virtually hidden. Each patient had very different volume CT dose index (CTDIvol), a measure of absorbed radiation. The obese patient (FIG. 2a) had a CTDIvol value of 67.2 milligrays (mGy), and the thin patient (FIG. 2b) had a CTDIvol value of 18.2 mGy. In spite of the increased x-ray fluence (67.2 mGy v. 18.2 mGy), the obese patient image still suffered from photon starvation. In the case of the obese patient, the therapists had increased the mAs to the maximum available by the clinical protocol.

CT simulation scanning, the acquisition of a CT scan for radiation treatment planning, is the first step in the radiation therapy workflow. CT simulation images are used to define tumor and normal organ anatomy by manual techniques or increasingly by use of commercial semi-automated or automated techniques. As previously stated, accurate tumor volume and normal organ segmentations are critical for maximizing dose conformality. Accurate segmentation relies on tumor and critical structure CT conspicuity, interpretation of radiological anatomy, and understanding of the potential areas of tumor involvement based on tumor biology with a main assumption that target segmentation based on CT simulation scans provides an accurate patient anatomy description. Diagnostic CT scanning protocols are driven by subjective image quality and radiation dose minimization as defined by the "as low as reasonably achievable" (ALARA) principle. However, one goal of radiation oncology CT simulation scans is to provide quantitative target and critical structure segmentation, which plays a critical role for accurate radiation treatment planning. In addition, the treatment-related normal organ dose received by most radiation oncology patients, even far from the tumor, greatly exceeds the dose from a CT simulation scan. Therefore, radiation oncology patients, especially obese patients, should not be subject to the same dose constraints as diagnostic imaging patients when those constraints compromise the accuracy of tumor and normal tissue segmentation. Up to now, methods for objectively optimizing CT simulation protocols to take into account radiation dose, patient size, and treatment planning requirements have not been developed.

Figure 1A:
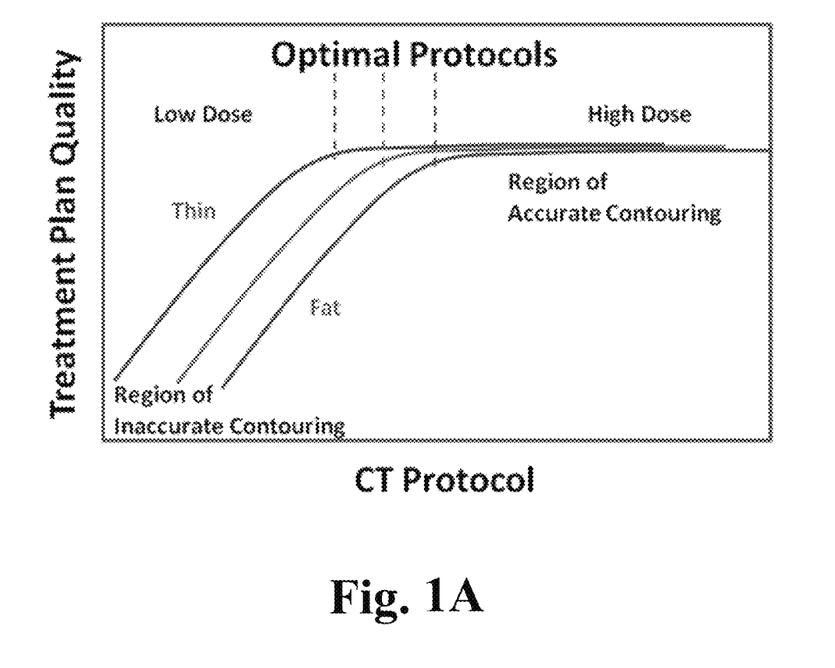
FIG. 1A is a chart illustrating the variation between the optimal CT protocols based on variation in size the patient.

The optimal CT simulation protocol is the one that delivers the minimum dose required to provide a CT simulation scan that yields accurate contours. Accurate treatment plans depend on accurate contours in order to conform the dose to actual tumor and normal organ positions. Previous diagnostic CT imaging studies have shown that a frequently employed method to manage CT image quality and radiation dose is to adjust the x-ray tube current using patient size or weight-based protocols. Also, the tradeoff between image noise and contrast enhancement determined the clinically optimal x-ray tube potential that yields the best image quality at the lowest radiation dose for a given patient size and clinical application. As shown in FIG. 1(a), low dose protocols yield lower image quality and cause inaccurate target contouring and poor treatment plans, which do not adequately cover the tumor or avoid the critical structures.

For sufficiently high dose protocols, the segmentation (or contouring) is accurate such that further increasing the technique only reduces image noise but has no impact on contouring and negligible impact on the resulting treatment plan and therapy dose distribution. Hence, for a given patient size, an optimal CT simulation protocol exists that delivers the minimum dose while providing a CT image data set that yields accurate contours, defined as contours that yield accurate treatment plans, conforming the dose to the actual tumor and normal organ positions.

SUMMARY OF THE INVENTION

The present invention addresses the problem associated with optimizing a CT simulation protocol for patients of different sizes. In connection with the present invention, a prediction method to determine the optimal CT simulation protocol for a patent size and treatment planning task is described. While treatment plan quality is the final arbiter of CT simulation scan quality, such a metric is impractical. Instead, an image quality index (IQI), defined to characterize contour delineation performance, is used to benchmark the contouring accuracy and treatment plan quality. To facilitate clinical use of the present invention, a workflow that automatically identifies the optimal CT simulation protocol for a given patient and treatment planning task is developed, taking into account the practical limits of CT scanning systems as well. The present invention uses a series of different sized, semi-anthropomorphic pelvis phantoms, cadavers or patients to demonstrate the potential of the inventive CT simulation optimization method for prostate cancer patients. Dosimetry comparisons are also used as part of the method to verify the inventive concept of optimizing CT simulation protocols. Such optimization of CT simulation protocols is achieved by first defining and then utilizing the IQI that acts as a surrogate linking the optimal CT simulation protocol to the contouring and treatment planning task. Development of IQI as an image quality metric allows for a straightforward optimal CT simulation protocol determination.

Figure 1B:
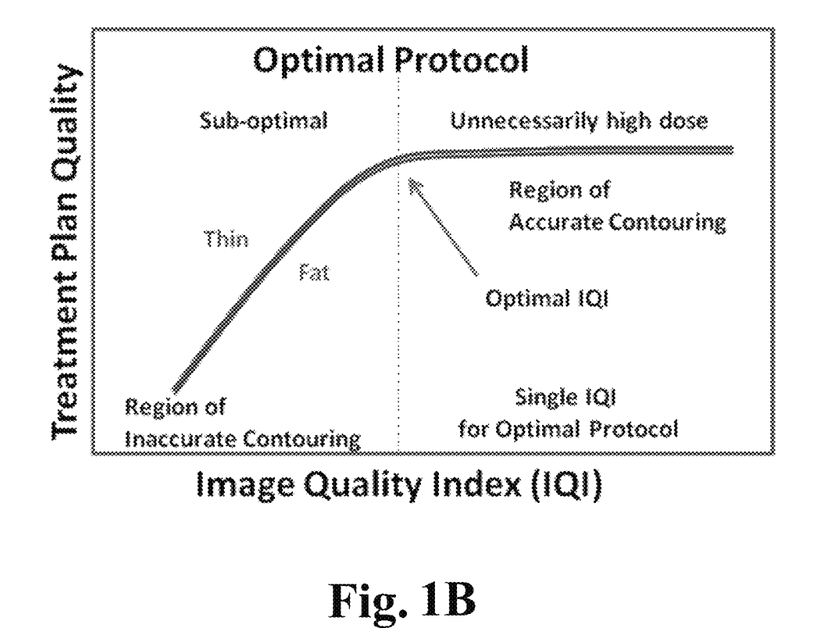
FIG. 1B is a chart illustrating the single the optimal CT protocol resulting from utilization of the present invention for patients with different size.

The definition of IQI should include all the factors affecting the contouring task and should be a single metric. The single metric reduces the image analysis dimensionality to one and simplifies the optimization selection process. The IQI directly connects the variation of image quality as a function of protocol to a quantitative value that is relevant to radiation therapy contouring. The contouring accuracy is related to segmentation techniques and treatment planning tasks. FIG. 1(b) summarizes the relationship between the treatment plan quality and IQI. For a given contouring technique and treatment planning task, a single IQI for all patient sizes exists, although the optimal protocols for different sized patients might yield different scan parameter settings in order to achieve the required image quality as established by the IQI.

Further objects, features and advantages will become apparent upon consideration of the following detailed description of the invention when taken in conjunction with the drawings and the appended claims.

BRIEF DESCRIPTION OF THE DRAWINGS

FIG. 3B is a CT anterior-posterior surview image of the phantom of FIG. 3a.

DETAILED DESCRIPTION OF THE PREFERRED EMBODIMENTS

While the detailed description of the invention that follows focuses on CT simulation scans and CT simulation protocols for patients having prostate cancer, the invention has applicability to all cancers that can be imaged by CT scanning and are treated by radiation therapy.

Medical Imaging Quality

The methodologies used to assess medical imaging quality, including images created by CT scanning, can be divided into two categories. The first is based on traditional physical measures of image quality including noise, spatial resolution, contrast, and signal-to-noise ratio (SNR). These measures have limited use with system optimization studies because they do not directly relate to a task. For example, two different images can possess the same SNR but have very different correlation structures, which can greatly affect signal detection performance. The noise power spectrum (NPS) describes both the magnitude and spatial frequency characteristics of image noise and is a more thorough noise descriptor than pixel standard deviation. However, NPS does not carry information of other intrinsic CT scan properties, such as focal spot size and detector width, which are carried by the modulation transfer function (MTF) instead. The noise equivalent quanta (NEQ) characterizes the signal and noise associated with image acquisition parameters for a CT scanner by combining NPS with MTF as $NEQ(u,v) = SNR_{out}^2(u, v) = MTF^2(u, v)/NNPS(u, v)$, where $(u, v) \in R^2$ and NNPS is the normalized NPS to the background signal level S, $NNPS(u, v) \equiv NPS(u, v)/S^2$.

Defining Image Quality Index—IQI

The second and more powerful approach to image quality assessment employs task-based measures that measure image quality as the average performance of a specified observer on a specified task. Task-based measures of image quality, also referred to as objective measures, are fundamentally distinct from physical measures in that task-based measures of image quality are inherently statistical and are grounded in statistical decision theory. Computation of task-based measures of image quality requires knowledge of the statistical properties of an image, which corresponds to a realization of a stochastic process.

In connection with the present invention, a task-based image quality index (IQI) is defined by integrating the MTF and NNPS with a task function over the frequency domain. The task-based IQI is determined and is used to benchmark the target contouring and subsequent treatment planning accuracy for cancer patients. The task-based IQI is defined by the following equation (1).

$$IQI^2 = K^2 \int\int\int \frac{MTF^2(k_x, k_y, k_z)|\Delta f^2(k_x, k_y, k_z)|}{NNPS(k_x, k_y, k_z)} dk_x dk_y dk_z \quad (1)$$

In Equation (1), NNPS defines both the magnitude and spatial frequency characteristics of image noise. NNPS can be calculated by taking the average of the squared Fourier transform of a large number of noise images or regions within the images containing noise only. MTF carries information of intrinsic CT scan properties such as focal spot size and detector width. MTF is used as a spatial resolution metric and is used to evaluate the imaging performance metrics such as detective quantum efficiency (DQE), NEQ, and detectability index. The measurements and/or calculations of MTF are known it to a person of ordinary skill in the art. $\Delta f$ represents the Fourier-domain difference of contrast of a target to its background.

A more generalized equation for calculating IQI is as follows:

$$'IQI^2 = \int\int\int NEQ(k_x, k_y, k_z) W_{task}^2(k_x, k_y, k_z) dk_x dk_y dk_z = \quad (2)$$
$$\int\int\int \frac{MTF^2(k_x, k_y, k_z) W_{task}^2(k_x, k_y, k_z)}{NNPS(k_x, k_y, k_z)} dk_x dk_y dk_z$$

In Equation (2), the expression $W_{task}(k_x, k_y, k_z)$ is a task function defined based on the specific segmentation requirement for imaging the tumors and organs of a patient. Therefore, the expression $W_{task}(k_x, k_y, k_z)$ is a more generalized way of describing the task as compared to the more specific $\Delta f$ expression used in Equation (1).

Data Sets

In order to create initial data sets to determine the IQI, a phantom is employed and subjected to a series of CT scans. A phantom is employed in order to create the initial data sets. Initial or additional data sets, however, could be created by CT scans of cadavers or of a number of actual patients over time. Such data sets resulting from the scans of actual patients over time may serve to refine the determination of the IQI. The data sets are then used to calculate IQI, which in turn is used to identify the optimal CT simulation protocol for a prostate cancer patient. The phantom is an anthropomorphic pelvis phantom with added bolus layers to represent human prostate cancer patients of different sizes.

The prostate lies within structures of slightly lower CT number, and the main critical structures, bladder and rectum, are relatively straightforward to segment using CT scanning when the resulting CT image provides sufficient information for a segmentation technique. Image quality suffers in obese patients due to inadequate photon fluence and subsequent photon starvation, potentially degrading the segmentation of prostate and critical structures and yielding inadequate planning target volume (PTV) coverage and critical structure sparing.

The Phantom

Figure 3A:
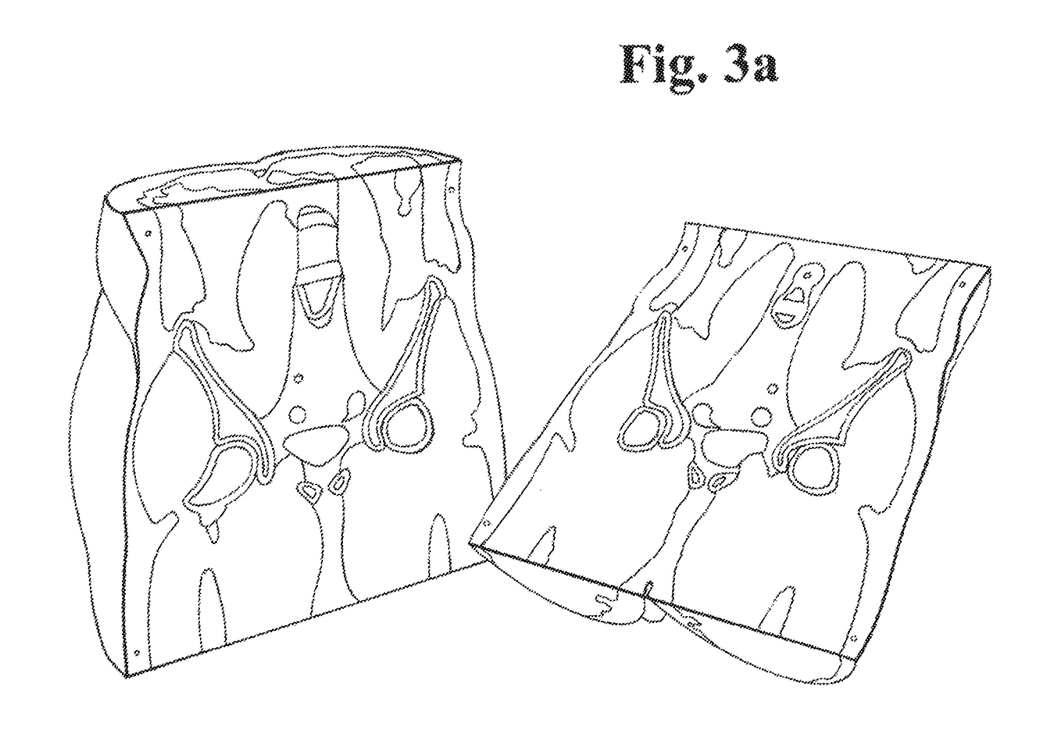
FIG. 3A is a photograph of an anthropomorphic human male pelvis phantom.
Figure 3B:
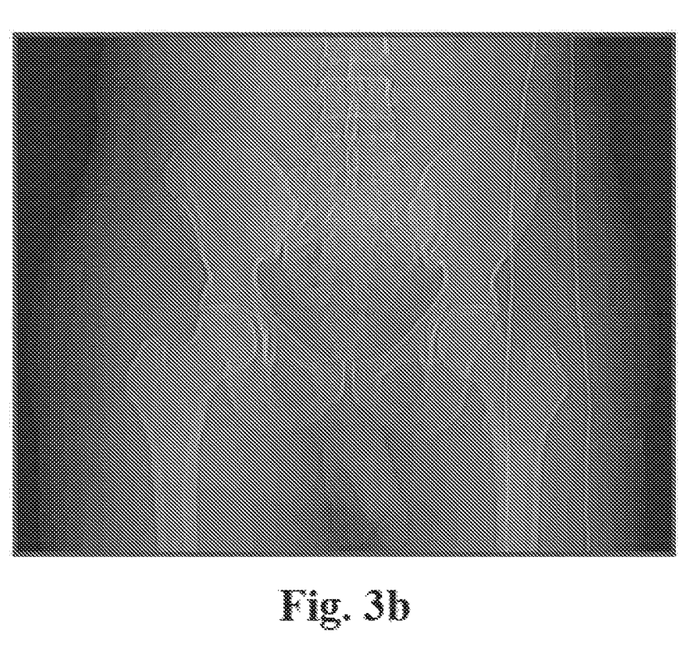

As shown in FIGS. 3a and 3b, an anthropomorphic human male pelvis phantom (manufactured and sold by CIRS Inc., Norfolk, Va.) with additional layers of attenuation is employed to simulate adult male patient with lateral diameters of 38 cm, 43 cm, 48 cm, 53 cm, and 58 cm. The pelvis phantom is made from proprietary epoxy materials that mimic human tissue density and radiation attenuation properties of human tissue within 1% from 50 keV to 25 MeV. The overall phantom dimensions are 38 cm wide, 26 cm thick, and 37 cm tall. The phantom contains anatomically precise bone, cartilage, spinal cord, vertebral disks, muscle, intestines, bladder, prostate, rectum, and interstitial fat. All anatomical dimensions of the phantom are based on the visible human project (VHP) data sets that serve as a reference for the study of human anatomy and are available through the National Library of Medicine. The additional attenuation layers, to mimic larger size patients, are provided by tissue-equivalent bolus material (Mick Radio-Nuclear Instruments, Inc. Mount Vernon, N.Y.), which is a synthetic oil gel with a specific gravity of 1.02, and based on vinyl plastic containing a large amount of di-isodecyl phthalate.

CT Scan Acquisition

CT scans of the phantom are acquired with a Philips Brilliance 64 slice CT simulator (Philips Healthcare, Cleveland, Ohio). To assure that the CT scans do not exceed the x-ray tube current limits of the scanner, a commercial 4DCT protocol is employed. The 4DCT protocol reduces the pitch to 0.06 and thereby provides mAs up to three to four times the standard helical protocol. The untagged 4DCT scans are reconstructed to simulate higher dose level helical CT scans and to generate a database for the implementation of the clinical method of the present invention. X-ray tube potentials lower than 120. (kilovolt peak) are not suitable for scanning even the smallest phantom size of 38 cm and certainly not for scanning any larger sizes due to higher tissue attenuation and lower human body penetration. Each size phantom is scanned with two x-ray tube potential settings, 120 kVp and 140 kVp. The x-ray tube current modulation function is disabled in order to evaluate the image quality under the full range of effective mAs. Other CT scan parameters include: 64×0.625 mm collimator setting, 0.5 second rotation time, a 0.06 pitch, standard resolution, standard B filter, 3-mm slice thickness, effective mAs/slice of 50, 100, 150, 200, 250, 500, 1000, 1500, 2000, 2500, and 3333 for 120 kVp CT scans, and mAs/slice of 50, 100, 150, 200, 250, 500, 1000, 1500, 2000, 2500, and 3000 for 140 kVp CT scans for each size phantom. The corresponding scanner radiation output, expressed as the volume CT dose index (CTDIvol) in the unit of mGy, is 3.3, 6.6, 9.8, 13.1, 16.7, 32.7, 65.4, 98.1, 130.8, 168.0, and 216.9 for 120-kVp CT scans and values in mGy of 4.9, 9.7, 14.5, 19.3, 24.7, 48.5, 97.0, 145.4, 193.9, 241.6, and 289.2 for 140-kVp CT scans for each size phantom.

The Data Sets and Data Processing

IQI is calculated with the acquired phantom data in a simplified way. $\Delta f$ in Equation (1) is simplified to the local contrast between prostate and its surrounding region. Because the contouring accuracy is measured locally, the combination of $\Delta f$ and NNPS is represented by the contrast-to-noise ratio of the local prostate to its local surrounding tissue region, and the CT image noise is measured within the local water-equivalent region surrounding the prostate. Because CT data sets are acquired from a single CT scanner using a single reconstruction kernel (filtered back projection, FBP) and a single standard filter, the effects from the local MTF are the same on all the images and are ignored. The theoretical definition of IQI is replaced by IQI(kV, RD, d), where kV is the CT scanner potential, RD is the radiation dose (represented by CTDIvol), and d is a patient size parameter. There are five different phantom lateral sizes of 38 cm, 43 cm, 48 cm, 53 cm, and 58 cm used in connection with the data acquisition. For each phantom size d, IQI(kV, RD, d), of the image acquired with a tube potential kV and radiation dose level RD, is calculated and used to generate an empirical prediction method for clinical practice.

First, the CT image of the 38 cm original phantom, scanned with 140 kVp and the greatest available CTDIvol of 289.2 mGy, is defined as the reference scan, in which five slices of the prostate region are selected. A set of contours outlining a uniform region of interest (ROI) within the prostate are defined on each slice. The average CT Hounsfield number and noise $\sigma$ (CT Hounsfield number standard deviation) for each ROI are measured. Additionally, the average CT Hounsfield number and $\sigma$ at the surrounding region outside the prostate ROIs are measured in the same way. The measurements, of which the sizes and relative locations of the ROIs drawn within the prostate and background region are kept consistent for all image sets and are used to calculate the simplified IQI of each image data set.

On each data set, the prostate, bladder, and rectum contours C(kV, RD, d) are manually delineated by an experienced dosimetrist and a trained medical physicist. The reference contour is defined as the manual prostate contour $C_{ref}$ delineated on the reference scan. Segmentation accuracy SA(kV, RD, d) of each data set is defined as SA(kV, RD, d)=(C(kV, RD, d)$\cap C_{ref}$)/$C_{ref}$, in which $SA_{ref}$=100% is the segmentation accuracy on the reference scan. Linear regression analysis is used to define the relationship IQI(kV, RD, d)=k(kV, d)/RD for each patient size d scanned at each tube potential kV. Once the coefficient k(k V, d) is determined, the coefficient k(k V, d) is used to determine RD with a given IQI(kV, RD, d). Again, linear regression analysis is used to determine a single coefficient $\lambda$ to represent the relationship between IQI(kV, RD, d) and SA(kV, RD, d) as SA(kV, RD, d)=$\lambda \cdot$IQI(kV, RD, d) for all patient sizes for a contouring technique. Because $\lambda$ only depends on the contouring tasks and techniques, the optimal IQI(d) required to reach accurate contour segmentation is determined once the $\lambda$ required to reach SA(kV, RD, d)=100% is determined for each patient sized at any kV and RD. Discrete tube potentials of 120 kVp and 140 kVp are used for CT simulation scans, and the CT scan protocol to achieve the optimal IQI(d) may be determined for each tube potential kV for a known IQI and d. The protocol requiring the lowest dose to achieve the optimal IQI(d), expressed as arg min RD(d, IQI(d), kV), is determined as the optimal scan protocol.

Clinical Implementation of the Invention

The clinical implementation of the invention uses a measurement of the patient size, which is the lateral diameter of the patient's body, as one input. A database of IQIs at each tube potential and radiation dose level using the phantom, cadaver, or patient data is created. For example and as previously described, the phantoms cover a variety of sizes that represent the attenuating characteristics of different patient sizes. For the patient exams, the optimal IQI is selected according to the required segmentation accuracy and treatment planning task for a measured patient lateral size and a predefined segmentation technique. The optimal IQI may vary for different segmentation techniques and treatment planning tasks. The optimal IQI, discussed below, results from the particular phantom scanning method of the present application and is therefore merely an example of an optimal IQI. Once the optimal IQI is selected, the optimal CT scanning protocol based on the experiments of the same sized phantom or using interpolation if necessary is selected. Below is the clinical workflow for automatically identifying the optimal CT simulation protocol parameters that are both dose efficient and practically feasible, incorporating patient size and target segmentation task.

(1) Acquire a CT radiograph (e.g., surview for Philips scanner, topogram for Siemens scanner, or scout for GE scanner). This is the basis for both automatic CT simulation protocol selection and automatic tube current modulation (if it is enabled).

(2) Measure the patient lateral size based on the selected contouring and treatment planning task. For example, if the contouring task is prostate segmentation for IMRT treatment planning, the lateral size will be measured on the pelvis region over the top of the femoral head.

(3) Determine the optimal IQI for selecting the optimal CT scan protocol for the measured patient size. Once the patient's lateral size is measured and the contouring and treatment planning tasks are selected, a software tool, described below, implemented from the phantom data automatically suggest a reference optimal IQI. The user can decide to utilize this suggested value or adjust it based on clinical practice. For example, based on the phantom data, the software tool recommends an optimal IQI 4.4 for the manual contouring task in the prostate IMRT treatment planning based on the phantom data. This value might not be clinically achievable for a large size patient due to x-ray tube limitations, lower IQI or even with additional noise constraints can be applied for clinical achievable protocol selections.

(4) Calculate the CT simulation protocol at each tube potential to achieve the defined optimal IQI. The amount of radiation that the system plans to deliver, expressed as CTDIvol, is reported as well. The optimal simulation protocol is the one that achieves the desired IQI while yielding the smallest CTDIvol value.

(5) With the optimal protocol and selected x-ray tube potential, adjust the mAs/slice (or effective mAs), rotation time, and/or pitch to yield the suggested minimum CTDIvol on the CT scanner. When automatic tube current modulation is enabled, adjust the rotation time, pitch, mAs, to match the maximum mAs/slice as that reported by the software tool. When automatic x-ray tube current modulation is disabled, adjust the rotation time, pitch, mAs, to match the mAs/slice as that reported by the software tool. Check the system limit and overall scan time to decide whether the dose level is achievable and clinically acceptable. If yes, then proceed with the optimal simulation protocol. If not, then select the highest achievable protocol for the scan. Such a process can be automatically conducted with the full knowledge of the CT system configuration.

Quantitative Software Tool

Figure 4:
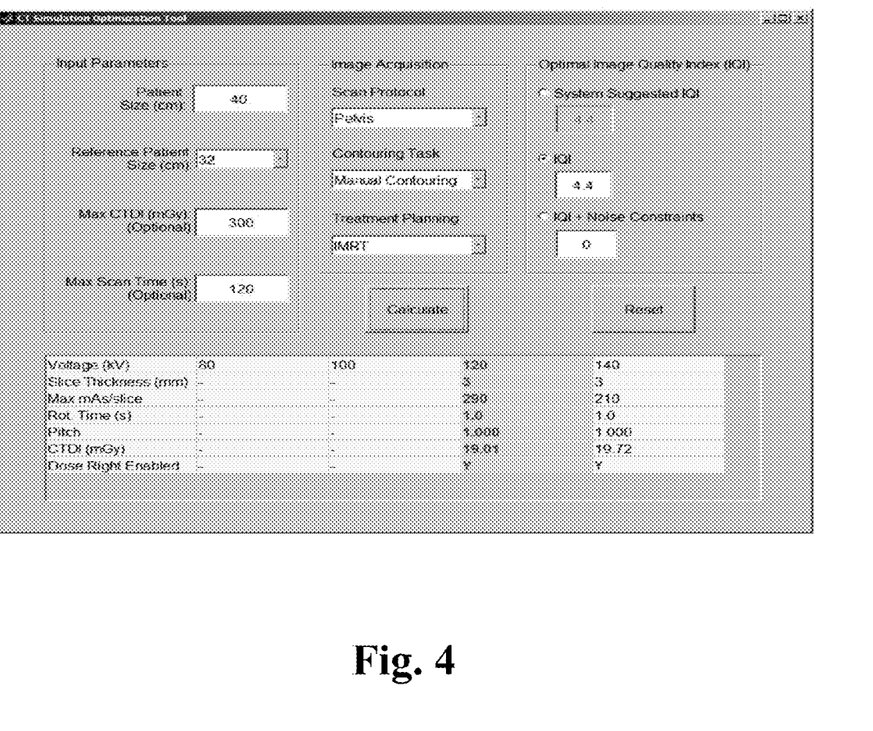
FIG. 4 is a representation of a computer interface screen showing a tool for automatic CT simulation optimization.

Based on the above-described phantom study and clinical workflow, a quantitative software tool can automatically select and implement the optimal CT simulation protocol. An interface for the software tool is shown in FIG. 4. Such a software tool is well within the capability of a person of ordinary skill in the art. Particularly, the current software tool is implemented with MATLAB.

The patient's lateral width provides an index of patient size. The IQI may use either predefined values recommended by the software tool based on the selected treatment planning task and contouring technique or adjusted values based on the practical requirements. With the parameters input on the left side of the panel, scan parameters and radiation dose at each x-ray tube potential to reach the desired IQI is calculated, and the final optimal CT simulation protocol is highlighted. A final check is then required to confirm that the pitch, scan time, and x-ray tube current values are within system limits.

Dosimetric Verification on Phantom Study

A quantitative dosimetry comparison is conducted on seven different dose level images for a 53 cm sized phantom to illustrate how the target contouring accuracy affected the treatment plan dose distribution and to verify that IQI may be used as a surrogate for CT simulation protocols and treatment planning accuracy. These seven varied dose-level images are all acquired with an x-ray tube potential of 140 kVp that yielded IQIs of 1.4, 2.0, 2.8, 3.4, 3.9, 4.4, and 4.8, respectively. An IQI of 4.4, based on image quality and minimum radiation dosage, is the optimal IQI for the data sets for the phantom scans. The prostate, bladder, and rectum contours are individually delineated on each image data set. IMRT prostate cancer treatment plans are optimized based on a consistent prescription. The prostate cancer IMRT planning protocol used seven 18-MV beams. The beams are distributed approximately evenly at angles around the patient but avoided entering through the high-density regions. The clinical target volume (CTV) is defined as the prostate contour, and the PTV is defined as the CTV plus a 5-mm isotropic margin. The maximum dose within the PTV is prescribed to be less than 110% of the prescription dose (7740 cGy). More than 98% of the PTV receives the prescribed dose or higher. 17% and 35% of the rectum volume is to receive treatment dose less than 6500 and 4000 cGy, respectively. 25% and 50% of the bladder volume is to receive a treatment dose less than 6500 and 4000 cGy, respectively. The clinical IMRT treatment plan, which is optimized on the reference scan with the reference contours, is used as the reference plan for comparisons with the seven test plans. The optimized treatment plans on each of the seven test images, including the dose prescription, beam geometry, and related parameters, are recomputed on the reference scan, and the resulting treatment plans are compared to the reference plan. With the seven recomputed dose distributions, the percentage PTV volumes receiving the prescription dose or higher, and the maximum doses within the PTV volumes are calculated and compared to the reference plan. The percentage rectum and bladder volumes receiving 6500 cGy or higher and 4000 cGy or higher of these seven recomputed dose distributions are calculated and compared to the reference plan as well. The γ dose distribution comparison tool is also calculated for each dose distribution pair to determine if the treatment plans generated using the different dose level CT scans fit the relationship expected in FIG. 1(b). The γ dose difference criteria are 3%, 2%, and 1% and the distance-to-agreement (DTA) criterion is 3 mm, resulting in three γ comparisons for each dose distribution pair. Dose areas with a γ value greater than 0.95 with 3%/3-mm DTA criterion are considered clinically equivalent.

Results

Figure 5:
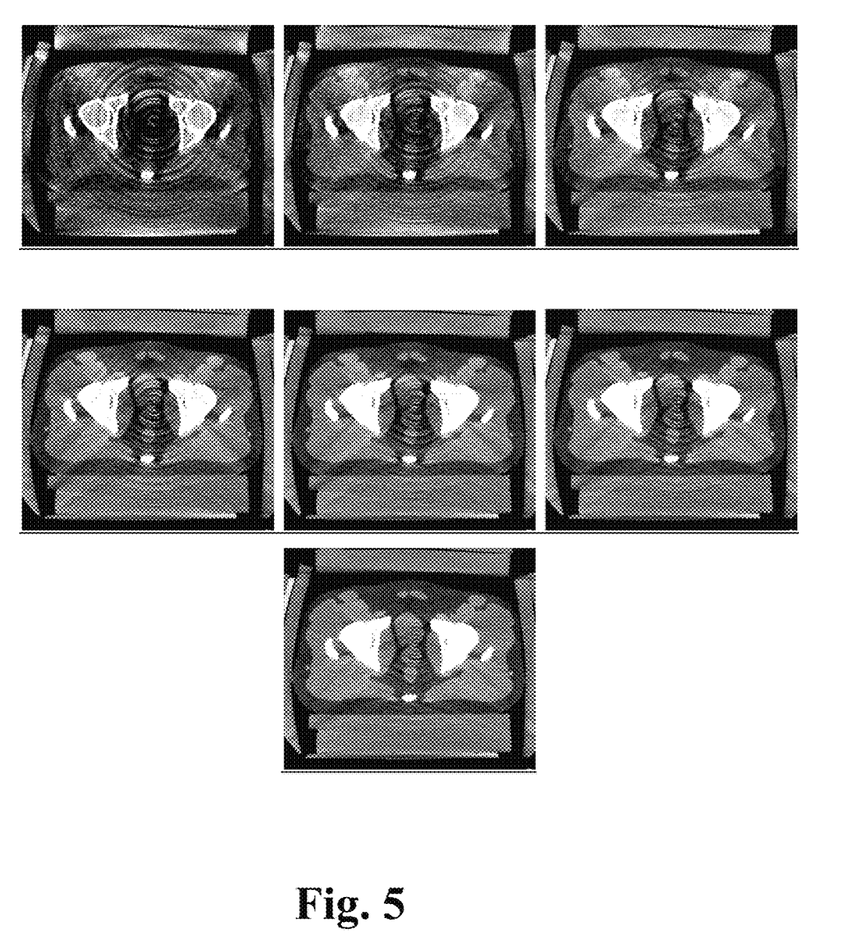
FIG. 5 shows a group of CT simulation images of an anthropomorphic pelvis phantom (with additional bolus to simulate a 53-cm pelvis diameter patient).

FIG. 5 shows an example of the impact of changing the effective mAs on image quality. CT simulation images of the anthropomorphic pelvis phantom with additional bolus to simulate a 53 cm pelvis diameter patient are acquired using 120 kVp scan protocols that varied only by x-ray tube current (mAs). The related CTDIvol values are 16.7 mGy, 32.7 mGy, 65.4 mGy, 98.1 mGy, 130.8 mGy, 168 mGy, and 217.0 mGy (left to right and top to bottom), respectively. The clinical routine pelvis protocol would deliver a CTDIvol of only 18.2 mGy, too low to obtain adequate image quality for prostate delineation and treatment planning for a patient this large.

Figure 6A:
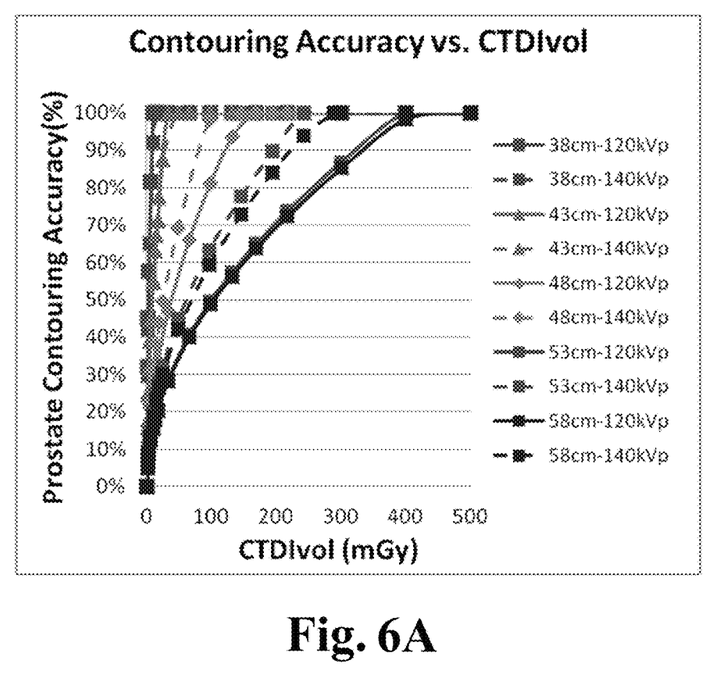
FIG. 6A is a graph showing the relationship of prostate contouring accuracy versus CTDIvol for manual prostate contouring.
Figure 6B:
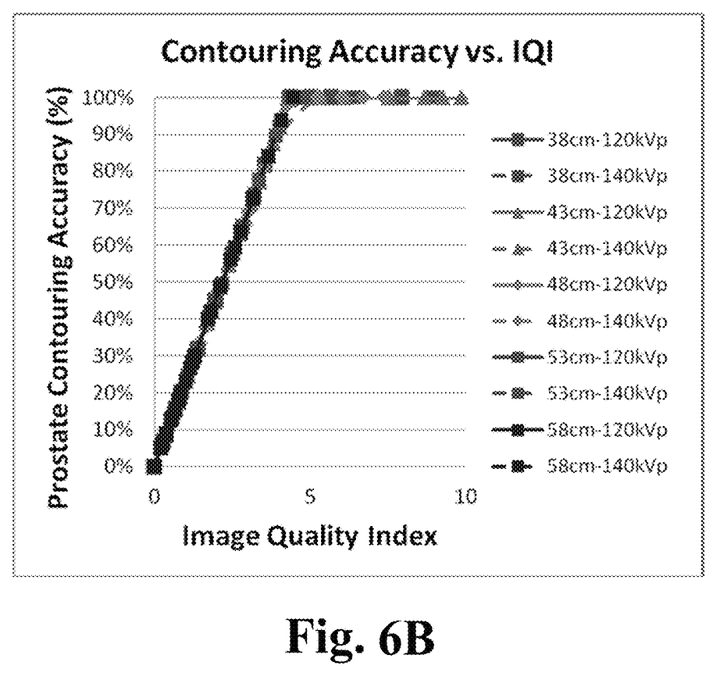
FIG. 6B is a graph showing the relationship of prostate contouring accuracy versus CTDIvol for IQI prostate contouring.

FIG. 6 shows the relationship between the manual prostate contouring accuracy to the radiation dose 6(a) and to the IQI 6(b) based on the phantom CT scans. Curve fitting is used to obtain the optimal IQI based on the phantom measurement. As shown in FIG. 6(b), the optimal IQI for accurate manual contouring is 4.4 for all patient sizes. The optimal tube potentials (yielding the lowest radiation dose) for patient sizes of 38 cm, 43 cm, 48 cm, 53 cm, and 58 cm are 120 kVp, 140 kVp, 140 kVp, 140 kVp, and 140 kVp, respectively, while the corresponding minimum CTDIvols for achieving the optimal IQI are 9.8 mGy, 32.2 mGy, 100.9 mGy, 241.4 mGy, and 274.1 mGy. Greater radiation dose protocols may be needed to achieve the same contouring accuracy for larger size patients. For patients with lateral sizes of 43-58 cm, 120 kVp CT scan protocols yielded more radiation dose, up to 165% of those from 140 kVp CT scan protocols, in order to achieve the optimal IQI.

Figure 7A:
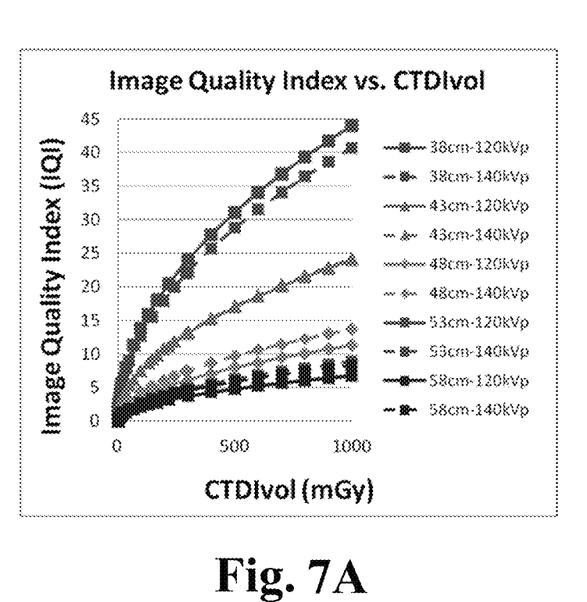
FIG. 7A is a graph showing the relationship of IQI versus CTDIvol for varying phantom sizes.
Figure 7B:
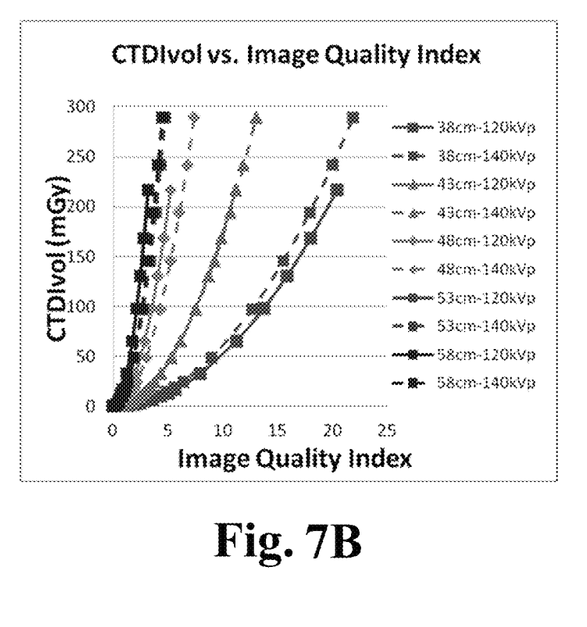
FIG. 7B is a graph showing the relationship of CTDIvol versus IQI for varying phantom sizes.

FIG. 7 shows the relationship of IQI to radiation dose for varied phantom sizes (38-58 cm) under two different tube potentials, 120 kVp and 140 kVp. As expected, the image IQIs increase with increasing radiation dosage. Greater dose protocols are required for larger phantoms in order to achieve the same IQI. For images of the 38 cm phantom, achieving the same IQI using 140 kVp protocols require greater radiation dosages than using 120 kVp protocols, but the situation is the opposite for larger phantom sizes (43-58 cm). For a 43 cm phantom, the IQIs of images scanned with both x-ray tube potentials are similar to each other using similar mAs. The larger the phantom size, the more dramatic the dose difference between x-ray tube potentials to achieve a similar IQI. For example, in order to achieve a 4.4 IQI for images scanned on the 38 cm phantom, the 120 kVp and 140 kVp protocols yielded CTDIvols of 9.8 mGy and 11.4 mGy, respectively. For images scanned using the 58 cm phantom, the 120 kVp and 140 kVp protocols required CTDIvols of 413.2 mGy and 274.0 mGy, respectively, to achieve the optimal IQI of 4.4. The reason is that an increasing amount of lower-energy photons are absorbed by the human body and increase the patient exposure but do not contribute to image formation. Table 1 shows the CTDIvol values that are required for all five sized phantoms at both 120 kVp and 140kVp CT scan protocols to achieve the optimal IQI.

TABLE 1

| | The required CTDIvol (mGy) | | | | |
|---|---|---|---|---|---|
| kVp | Phantom Size (cm) | | | | |
| Settings | 38 cm | 43 cm | 48 cm | 53 cm | 58 cm |
| 120 | 9.8 | 32.8 | 149.6 | 398.5 | 413.2 |
| 140 | 11.4 | 32.2 | 100.9 | 241.4 | 274 |

Figure 8A:
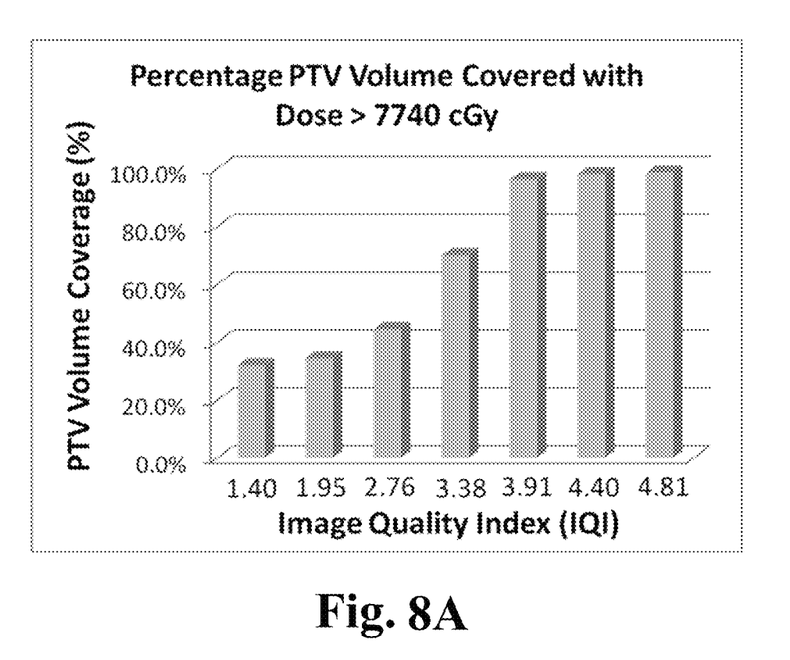
FIG. 8A is a graph showing the relationship of planning target volume (PTV) coverage versus IQI at a dose level of 7740 cGy.
Figure 8B:
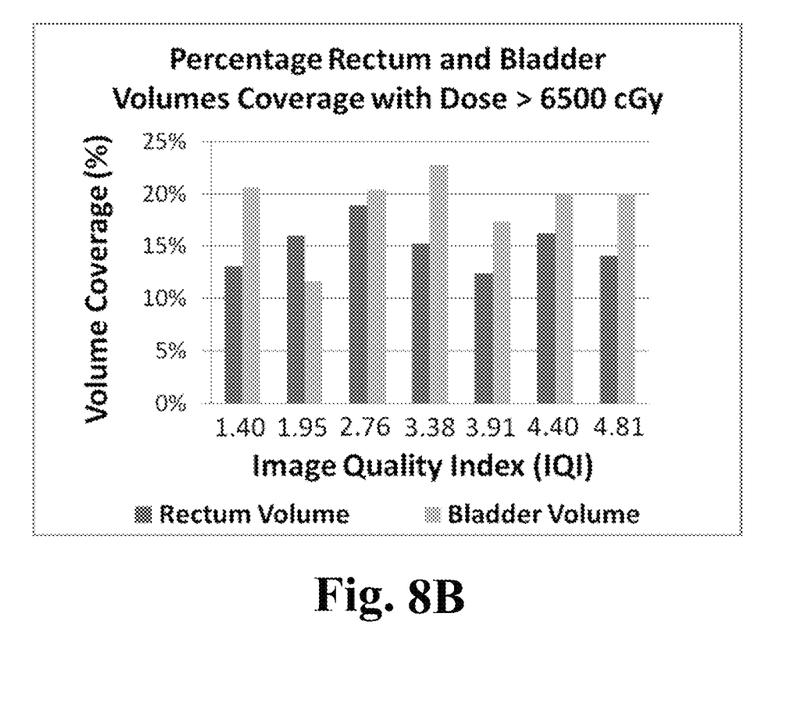
FIG. 8B is a graph showing the relationship of PTV coverage versus IQI for a rectum and a bladder at a dose level of greater than 6500 cGy.
Figure 8C:
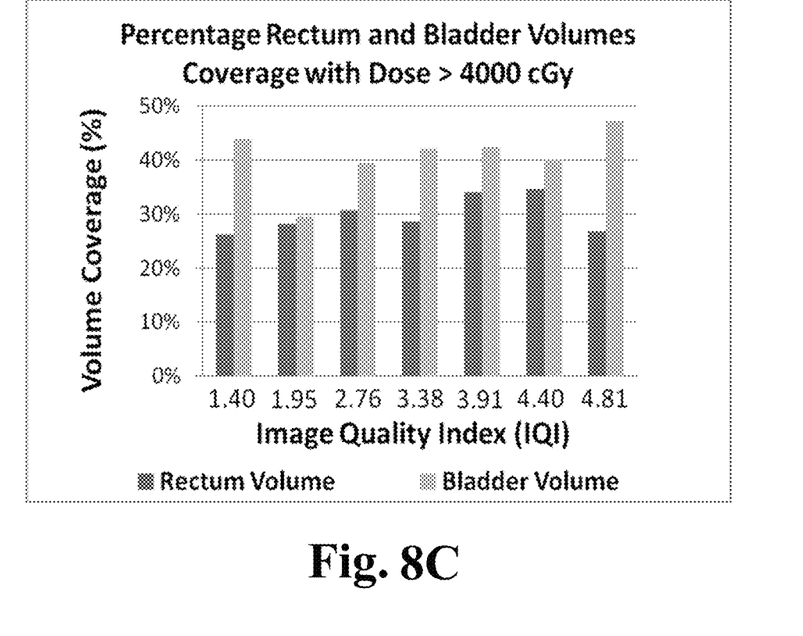
FIG. 8C is a graph showing the relationship of Volume Coverage versus IQI for a rectum and a bladder at a dose level of greater than 4400 cGy.
Figure 8D:
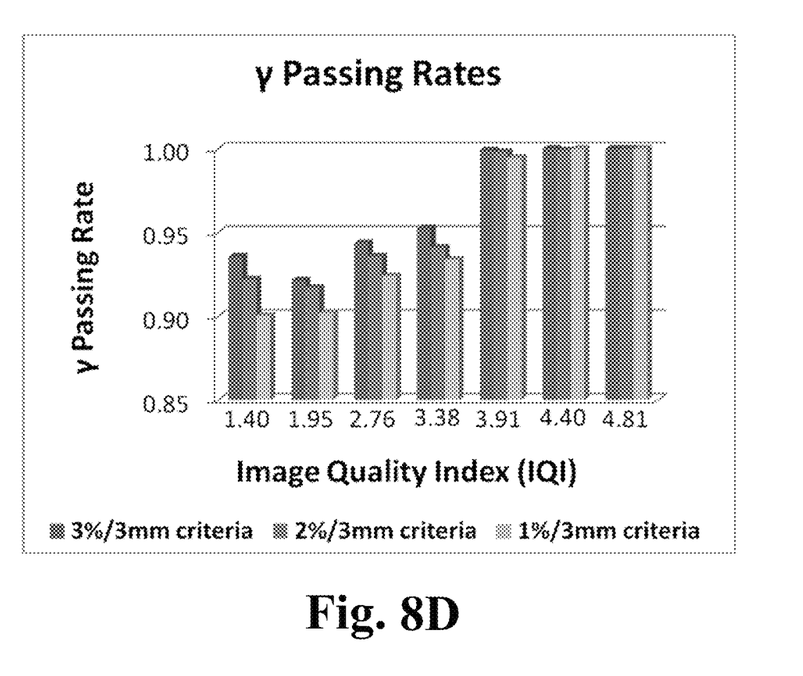
FIG. 8D is a graph showing the relationship of $\gamma$ passing rate versus IQI.

FIG. 8(a) illustrates the percentage PTV volumes receiving the prescription dose (7740 cGy) or higher of the seven recomputed dose distributions on the reference scan. The dose plans optimized on the higher quality images (with greater IQIs) still achieve greater PTV volume coverage (>98%), however, the dose plans optimized on the low quality images (with smaller IQIs) yielded poorer PTV coverage and are considered clinically unacceptable plans. FIGS. 8(b) and 8(c) illustrate the percentage rectum and bladder volumes receiving a dose of 6500 cGy or higher, and a dose of 4000 cGy or higher, respectively. An interesting finding is that most of these seven recomputed dose distributions still satisfied the bladder and rectum dose limits, and the differences between the dose plans optimized on images with varied IQIs are small. FIG. 8(d) details the comparison of γ passing rates of each dose distribution pair in the entire dose grid. Three dose plan pairs for the images with higher IQI 3.9, 4.4, and 4.8 yielded γ passing rates of greater than 0.99, so the dose distributions are considered clinically equivalent. The remaining four dose distributions with lower IQIs (1.4-3.4) yield γ passing rates of less than 0.95.

Figure 9A:
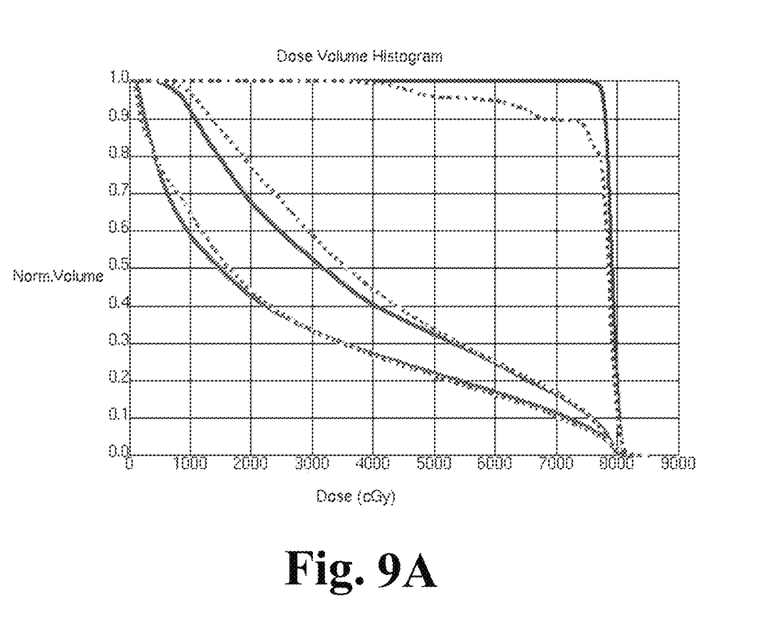
FIG. 9A is a histogram showing the distribution for the PTV, bladder, and rectum for an IQI of 1.4.
Figure 9B:
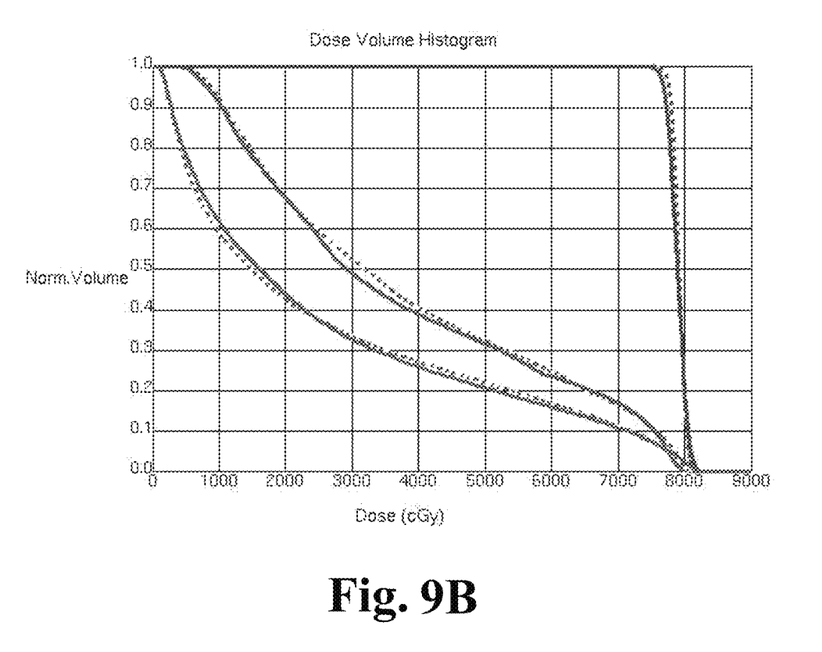
FIG. 9B is a histogram showing the distribution for the PTV, bladder, and rectum for an IQI of 4.4.

FIG. 9(a) compares the dose volume histograms (DVH) of the PTV, rectum, and bladder of the reference plan and the resulting IQI 1.4 dose plan that recomputed onto the reference scan and reference contours. Even though the prostate has relatively high CT image contrast, only 32% of the PTV received at or above the prescription dose, which is much lower than the required 98%. FIG. 9(b) shows a similar comparison, this time with the 4.4 IQI plan. In this case, the PTV dose distributions are similar, with γ passing rates greater than 0.999 using 3%, 2%, and 1% with 3 mm DTA criteria, indicating that CT scans with the optimal IQI 4.4 may be considered as a clinically equivalent to the reference scan.

Summary

The present invention is a general prediction method that identifies CT simulation protocols as a function of patient size and radiation treatment planning task. There are three main aspects of the invention. First, the idea of dose in CT simulations is re-examined, especially for obese patients. As shown in FIG. 6, if the routine clinical 120 kVp pelvis protocol (yielding CTDIvol of 18.2 mGy) is used to scan the 53 cm lateral sized phantom, such a routine protocol leads to about 20% prostate segmentation accuracy, and only about 32% of the PTV volume is covered with prescription dose or higher. Rather than subjectively pushing the radiation dose either up or down, the present invention objectively justifies the CT simulation protocol for each patient based on quantitative image quality predictions and ultimately improves the quality of radiation therapy treatment planning. In this way, target contouring and subsequently treatment planning accuracy for obese prostate cancer patients is enhanced. Moreover, for thin patients, determination of the image quality that is sufficient to accomplish a given treatment planning task may actually facilitate lowering of imaging doses. While the treatment dose prescribed for radiotherapy is far greater than imaging doses, the dual goals of CT simulations for radiation treatment planning are target and normal tissues delineation optimization and patient exposure minimization. Unnecessary radiation dose to patients from imaging devices should always be avoided.

Second, while treatment plan quality is the final arbiter of CT simulation quality, using treatment plan quality as a metric CT simulation optimization is impractical. The present invention instead employees the IQI to take into account the requirements on CT image quality for a given treatment planning task and to serve as a benchmark for radiation treatment plan quality. The use of IQIs reduces the image analysis dimensionality to one and directly connects the variations of image quality as a function of CT simulation protocols to a quantitative value that is relevant to radiation therapy segmentation. Different optimal IQIs may be required for manual target segmentation and automatic segmentation techniques in order to achieve the same target segmentation accuracy. Many automated segmentation techniques, such as atlas-based methods, simultaneously access the entire three-dimensional data set for segmentation. Therefore, the target contouring accuracy may be improved when using automated segmentation techniques.

Third, in order to generate a complete phantom data set for morbidly obese patients, protocols are used for the acquisition of high effective mAs CT scans. Ungated 4DCT protocols are utilized to generate high dose CT simulation images. As shown in FIG. 6(a), higher radiation dose protocols are required for achieving the optimal IQI for larger sized patients. Due to the tube limitations and patient dose concerns, dose-reduced CT scan protocols for the clinical practice are utilized. For example, automatic exposure control (AEC) techniques may be used to reduce the radiation dose while keeping the required image quality. AEC automatically adapts the x-ray tube current as the x-ray tube rotates around the patient and as the patient travels through the scan plane, adjusting the current according to patient size to keep image noise or quality constant. This approach can achieve a dose reduction of 40%-50% without sacrificing the image. Moreover, there have been several physics and clinical studies on the optimization of x-ray tube currents and x-ray tube potentials in CT imaging with the purpose of improving image quality or further reducing radiation dose for diagnostic CT scanning. These previous methods may be employed to refine the prediction allmethod of the present invention and to reduce the radiation dose further while maintaining the image quality satisfying a treatment planning task.

As shown in FIG. 8, although the γ passing rate of the IQI value of 3.9 dose plan and the reference dose plan pair is greater than 0.99, only 96.3% of the PTV volume is covered with prescription dose or higher, which is slightly lower than the required 98%. The large variations of PTV volume coverage are mainly due to the contour variations. PTV and normal organ dose coverage should be considered together with the γ dose distribution comparison tool for the dose distribution equivalence comparisons. CT simulation protocols should be optimized based on both target contouring accuracy and radiation dose efficiency instead of directly duplicating the protocols for diagnostic imaging. During the clinical implementation, the user may need to adjust the appropriate scan parameters such as pitch, rotation time, and slice thickness to match the practical requirements. For example, if the scan requires the patient to hold his or her breath, the total scan time should be shortened as much as possible by increasing the pitch and/or lowering the rotation time while keeping the required dose level. The x-ray tube power limit is also a factor to consider during the protocol selection process, especially for scanning obese patients. The experimental results show that even the maximum dose available 120 kVp and 140 kVp protocols could not achieve the optimal IQI for 58 cm or larger sized patients due to the x-ray tube power limits. The user may need to allow a higher noise level for larger sized patients. These selections can be set up beforehand for each scanning protocol. Although the IQI provides a flexible way to balance between favoring strong object contrast and maintaining reasonable noise properties, other issues, such as beam-hardening artifacts and electronic noise can still influence CT scanning results. More x-ray beam-hardening artifacts occur at lower kV than at higher kV for bigger phantoms. In a practical implementation of the proposed strategy, artifacts caused by x-ray beam-hardening, photon starvation, and other factors should be considered as well. New iterative reconstruction algorithms, such as Philips iDose4 algorithm, may be utilized to achieve better image quality for large sized patients. However, the definition of IQI may require further investigations because the definitions of MTF and NPS assume a linear and shift-invariant system while iterative reconstruction is typically nonlinear.

The optimization method of the present invention is easy to be adapted to another CT scanner or another institution. The general optimization method the same, but the optimal IQI and CT simulation protocols may vary. The reasons are (1) the CT image quality and radiation dose is scanner dependent and (2) the optimal IQI is dependent to segmentation techniques and treatment planning tasks. The optimal IQI and CT simulation protocols should be verified for each translation through phantom study or possible patient study. The simplified IQI definition disclosed herein can also be translated to other scanners while keeping the same contouring technique, treatment planning task, and other assumptions. Similarly, verifications with a phantom study are necessary for translating the simplified IQI to other CT scanners. In this study, CTDIvol is used to represent the radiation dose, and in conjunction with the information regarding patient size and scanned anatomy, to predict the optimal CT simulation protocols. CTDIvol provides a very useful way to compare the doses delivered by various scan protocols or to achieve a desired level of image quality for a specific sized patient. However, such doses are measured with two standard sized phantoms on CT scanner output without taking into account patient size, shape, composition, and scan length. As such, CTDIvol does not represent the radiation dose to a real patient. Even though it is sufficient to use it as an index for selecting optimal protocols for the current study, the users should be aware of its intrinsic properties and limitations.

While this invention has been described with reference to preferred embodiments thereof, it is to be understood that variations and modifications can be affected within the spirit and scope of the invention as described herein and as described in the appended claims.

We claim:

1. A method for optimizing a computed tomography (CT) simulation protocol for different size patients for contouring and segmentation of organs and tumors comprising:
   a. scanning different size phantoms, cadavers, or patients with a CT scanner to create a set of CT images, wherein CT scanning parameters are varied to create CT image data sets for each different sized phantoms, cadavers, or patients and wherein radiation output of the CT scanner is recorded;
   b. calculating image quality indices (IQI) based on the CT image data sets,
   c. selecting an optimum IQI from the IQI indices based on the contouring quality of CT images in the CT image data sets and on minimizing radiation output that produces the CT images; and
   d. creating a contouring CT simulation protocol for a particular patient including CT scanning parameters, wherein the CT scanning parameters for the contouring CT simulation protocol for the particular patient result in the optimal IQI.

2. The method of claim 1, wherein using the contouring CT simulation protocol on additional patients over time produces additional CT images and CT image data sets that are used to further define the optimal IQI.

3. The method of claim 1, wherein the IQI is calculated based on the CT image data sets and wherein the IQI is calculated in accordance with the following formula:

$$IQI^2 = \int\int\int NEQ(k_x, k_y, k_z)W_{task}^2(k_x, k_y, k_z)dk_xdk_ydk_z = \int\int\int \frac{MTF^2(k_x, k_y, k_z)W_{task}^2(k_x, k_y, k_z)}{NNPS(k_x, k_y, k_z)}dk_xdk_ydk_z$$

wherein:
a. the expression $MTF^2(k_x, k_y, k_z)$ is a transfer function that carries information of intrinsic CT scan properties;
b. the expression $W^2_{task}(k_x, k_y, k_z)$ is a task function defined based on segmentation requirements; and
c. the expression $NNPS(k_x, k_y, k_z)$ is the normalized noise power spectrum to background signal level.

4. The method of claim 1, wherein the IQI is calculated based on the CT image data sets and wherein the IQI is calculated in accordance with the following formula:

$$IQI^2 = K^2 \int\int\int \frac{MTF^2(k_x, k_y, k_z)|\Delta f^2(k_x, k_y, k_z)|}{NNPS(k_x, k_y, k_z)}$$

wherein:
a. the expression $MTF^2(_x, k_y, k_z)$ is a transfer function that carries information of intrinsic CT scan properties;
b. the expression $\Delta f$ represents the Fourier-domain difference of contrast of a target to its background; and
c. the expression $NNPS(k_x, k_y, k_z)$ is the normalized noise power spectrum to background signal level.

5. The method of claim 1, wherein the CT scanning parameters for acquiring the CT images include collimator setting, rotation time, pitch, resolution, filter, slice thickness, x-ray tube current, x-ray tube potential, and radiation output.

6. The method of claim 1, with automatic tube current modulation enabled on the CT scanning x-ray tube, adjusting the rotation time, pitch, and effective amperage, to match the maximum amperage/slice of the CT simulation protocol.

7. The method of claim 1, with automatic tube current modulation disabled on the CT scanning x-ray tube, adjusting the rotation time, pitch, and amperage, to match the amperage/slice of the CT simulation protocol.

* * * * *